(12) United States Patent
Neuhann

(10) Patent No.: US 6,494,857 B1
(45) Date of Patent: Dec. 17, 2002

(54) DEVICE FOR IMPROVING IN A TARGETED MANNER AND/OR PERMANENTLY ENSURING THE ABILITY OF THE AQUEOUS HUMOR TO PASS THROUGH THE TRABECULAR MESHWORK

(76) Inventor: Thomas Neuhann, Herzogstr. 48 80801 Munich (DE)

( * ) Notice: Subject to any disclaimer, the term of this patent is extended or adjusted under 35 U.S.C. 154(b) by 0 days.

(21) Appl. No.: 09/786,282
(22) PCT Filed: Aug. 17, 1999
(86) PCT No.: PCT/DE99/02588

§ 371 (c)(1),
(2), (4) Date: Jun. 4, 2001

(87) PCT Pub. No.: WO00/13627
PCT Pub. Date: Mar. 16, 2000

(30) Foreign Application Priority Data

Sep. 2, 1998 (DE) .......................................... 198 40 047

(51) Int. Cl.⁷ .............................. A61M 5/00; A61F 2/14
(52) U.S. Cl. ............................................. 604/8; 623/4.1
(58) Field of Search ............................... 623/4.1; 604/8, 604/294, 264

(56) References Cited

U.S. PATENT DOCUMENTS 4,936,825 A * 6/1990 Ungerleider ................. 604/294
5,360,399 A * 11/1994 Stegmann ..................... 604/28
5,868,697 A * 2/1999 Richter et al. ............... 604/294

FOREIGN PATENT DOCUMENTS

WO    WO 95/08310    * 3/1995    ............. A61F/9/00

* cited by examiner

Primary Examiner—Paul B. Prebilic
Assistant Examiner—William H Matthews
(74) Attorney, Agent, or Firm—Antonelli, Terry, Stout & Kraus, LLP

(57) ABSTRACT

A device is disclosed for selectively improving and/or permanently ensuring the permeability for ocular aqueous humour through the trabecular formations into Schlemm's canal. A small tubular element is provided, whose wall material encloses a hollow duct that presents an open configuration on both ends along the longitudinal extension of the hollow duct, so that the size and the shape of the small tubular element correspond approximately to the internal contour of Schlemm's canal, and the wall material as well as the wall thickness are so selected that upon introduction into Schlemm's canal the small tubular element keeps the canal open and dilates adjacent trabecular formations.

29 Claims, 3 Drawing Sheets

DEVICE FOR IMPROVING IN A TARGETED MANNER AND/OR PERMANENTLY ENSURING THE ABILITY OF THE AQUEOUS HUMOR TO PASS THROUGH THE TRABECULAR MESHWORK

BACKGROUND OF THE INVENTION

1. Field of the Invention

The present invention relates to a device for selectively improving and/or permanently ensuring the permeability for ocular aqueous humour through the trabecular formations into Schlemm's canal.

2. Description of the Prior Art

In cases where the aqueous humour cannot escape from the intra-ocular cavity sufficiently the intra-ocular pressure increases, which intensifies the risk of formation of glaucoma. The glaucoma is a particular form of optic nerve atrophy that is predominantly induced by an intra-ocular pressure too high for a healthy functioning of the nerve.

As a consequence, the reduction of the intra-ocular pressure at least to values within the limits of statistical normal (statistical WLN) is the primary aim of any therapeutic approaches in glaucoma treatment.

The reduction of the ocular pressure can be achieved by a number of medicaments, by laser methods in so-called argon laser trabeculoplasty (ALT) or by surgical procedures in a fairly narrow sense. Disadvantages entailed by a therapy based on medication are an only restricted pressure reduction potential, undesirable side effects and, above all, the necessity of life-long application several times a day, which involves naturally problems of reliable application (compliance).

Disadvantages entailed by argon laser trabeculoplasty are their reduced pressure reduction potential and their only transient efficacy as the effect is reduced in the course of time.

Among the surgical procedures the so-called firstling techniques are the operative standard today. Among their numerous disadvantages, the substantial potential of post-operative complications should be particularly emphasized, apart from the accelerated formation of a cataractous lens, the unpredictability of the effect that may range from excessive reduction of the pressure up to a rapid cicatrizationg with an entire loss of the pressure-reducing effect.

This entirely unsatisfactory balance of success and the insufficient predictability of the success of this standard procedure has resulted in a great number of other surgical approaches among which the trabeculotomy and the deep sclerotomy should be mentioned particularly, which are both surgical techniques permitting a facilitated outflow of the aqueous humour by the provision of physiologic excretory or drain ducts. These techniques, too, involve, however, the particular disadvantage that their effect may be lost again, either partly or entirely, as a result of wound healing processes.

The following explanations are intended to facilitate the understanding of the glaucoma problems:

The space between the crystalline lens and the posterior cornea surface, which is subdivided by the iris into the posterior and the anterior chambers of the eye, is filled with aqueous humour. The aqueous humour is permanently produced by the ciliary body, the corpus ciliare, of the eye and is discharged into the posterior chamber of the eye. The aqueous humour then flows from there through the pupil into the anterior chamber of the eye, where it is subjected to a heat flow, and arrives from there into the iridocorneal angle through the meshwork of the corneoscleral trabecular formations into Schlemm's canal, also referred to as the venous sinus of the sciera. The aqueous humour finally flows from there through excretory ducts into the venous system of the eye surface.

The secretion and outflow of the aqueous humour in a homeostatic balance serves the purpose of maintaining an intra-ocular pressure at a constant level within narrow limits, which must, however, be sufficiently high in order to retain the dimensional stability of the eye, and low enough in order to avoid any obstruction of the nutrition of the optic nerves. Values within the range from 10 mm Hg to 20 mm Hg are roughly considered as standard range for the intra-ocular pressure. There is, however, no clear distinction between normal values and increased pathological values: the transition is fluid, with an ever-increasing probability of a glaucoma disease as the levels of the intra-ocular pressure are rising.

A pathological increase of the intra-ocular pressure may fundamentally be caused by both excessive secretion of aqueous humour and insufficient outflow. For the purposes of the present description only the increase of the outflow obstruction in the juxta-canalicular trabecular formations will be discussed here, which constitutes the basis of the so-called primary chronic glaucoma simplex, which obstruction is quoted in the scientific literature as accounting for 85 to 90% approximately of all of these glaucoma constellations.

The chronic glaucoma simplex accounts, in its turn, for more than three quarters of all glaucoma cases. The causes of this increase of resistance in the juxta-canalicular trabecular formations are, in the last analysis, not clarified in all details. Genetic factors, the deposition of substances on the meshwork with a restriction of the mesh aperture and hence an increase of the resistance, as well as a mechanical collapse of the meshwork are aspects deemed to be established facts.

The principle of trabeculotomy as applied nowadays is as follows: Starting out from the trabeculotomy technique known per se, Schlemm's canal is located and opened from outside. Then a metal probe is introduced into the canal and pivoted into the anterior chamber. Such an operation actually tears the trabecular formations in their entirety, however, so that an open communication is established between the anterior chamber of the eye with the aqueous humour circulating therein and Schlemm's canal.

The anatomic structure of the trabecular formations, where the increased outflow obstruction is located, is, however, actually destroyed by the aforedescribed approach. Even though this surgical method initially furnished only hardly convincing results it gained importance substantially throughout the past few years due to refined techniques. There is no other method, for instance, by which the pressure-reducing success produced by this approach has been achieved under certain conditions. It involves, however, the inherent problem that the two ends of the opened distance may close again so that only the actually torn-up passage, rather than the entire canal range, is available for outflow.

To this adds the aspect that the torn-up trabecular formations may conglutinate again in certain cases as the two torn-up parts of the trabecular formations are closing, so to speak in the manner of the wings of a door. Such resealing is promoted by reflux bleeding from the venous system communicating with Schlemm's canal.

The European Patent EP 0 550 791 A1, for instance, discloses a surgical instrument specifically configured for the selective injection of a highly viscous medium into the trabecular formations. This instrument is, in particular, a surgical probe that is introduced into Schlemm's canal during the operation and subsequently removed completely from this canal after the treatment.

The probe with its arcuate configuration presents openings on the internal side of the arc, through which the highly viscous medium is injected into the trabecular formations. To this end the curved probe is connected to an injection introduced into Schlemm's canal. A detailed representation of this mode of operation of the injection procedure is apparent from FIG. 2.

The known device constitutes a surgical instrument for performing a surgical procedure on the eye for local dilation of the trabecular formations by selective injection into this system in an approach to improve its permeability to the aqueous humour.

A comparatively small opening in the trabecular formations would, in principle, be sufficient to permit the desired effect of intra-ocular pressure control if it could be ensured that the opening will not be closed again so that the aqueous humour will gain access through this gap, even though this gap is admittedly small, to Schlemm's canal in its entirety and hence to the natural outflow system. After a treatment of the trabecular formations with the techniques so far known it is not possible, however, to prevent artificial perforations or dilations in the trabecular formations from being closed again by natural deposits, so that the principal cause of glaucoma occurrence does not seem to be eliminated on a long-term basis.

SUMMARY OF THE INVENTION

The present invention is based on the problem of finding a solution to the aforedescribed problems in the performance of surgical operations for glaucoma treatment and specifically for the restoration of a purposeful control of the intra-ocular pressure to the effect that re-sealing of passage ducts established in the trabecular formations should be avoided entirely. In particular, the traumatic irritations of the tissue within the trabecular formations should be reduced, which would also improve the wound-healing process. Eventually, the inventive provisions should contribute to a fundamental increase of the permeability even without any lesion in the trabecular formations.

In accordance with the present invention, a device for selectively improving and/or permanently ensuring the permeability for ocular aqueous humour through the trabecular formations into Schlemm's canal is configured in such a way that a small tubular element is provided, whose wall material encloses a hollow duct which presents an open configuration on both ends along the longitudinal extension of the hollow duct, that the size and the shape of the small tubular element correspond approximately to the internal contour of Schlemm's canal, and that the wall material as well as the wall thickness are so selected that upon introduction into Schlemm's canal the small tubular element will slightly deform, preferably dilate, i.e. expand, this canal as well as the adjacent trabecular formations.

The present invention is based on a small tube, a so-called stent, being introduced into Schlemm's canal. This stent serves the purpose of spreading the trabecular formations on an internal side and hence reducing the outflow obstruction. The stent is manufactured of a material compatible with the body tissue and stays insides Schlemm's canal even after the operation in order to dilate the latter permanently.

When this reduction of the outflow obstruction is not sufficient, the stent additionally permits the opening or removal of the trabecular formations on its permeable side facing the trabecular formations, while it preventing the opening in the trabecular formations from re-sealing and Schlemm's canal from conglutinating.

The aqueous humour is hence given unobstructed access to the entire circumference of Schlemm's canal and its excretory ducts. In order to satisfy these demands it is necessary to manufacture the small tube or stent from an appropriate material having an external shape that corresponds largely to the internal shape of Schlemm's canal or that shapes this canal anew. Moreover, the small tube presents a hollow duct inside which leaves just enough wall thickness for reliably preventing the stent from collapsing.

The small tube may fundamentally have any length; it is expedient that the length of the small tube corresponds to not less than 30° and not more than 90° of the radian measure of Schlemm's canal having a circular extension. Other lengths and their sensible application are, however, conceivable in principle.

The small tube preferably presents a curvature corresponding to the curvature of Schlemm's canal in the eye under operation. The small tube must hence be manufactured either in an individualized manner or in a standardized form.

The small tube is permeable to liquids at least on the concave side of the curvature while stretching the tissue and keeping the canal open. This is the side that faces the trabecular formations and the anterior chamber of the eye directly in the implanted state. The small tube presents preferably openings in the wall material on this side, but the small tube may also be made of a wall material that is inherently permeable. As an example, braided materials with finite wide or small mesh apertures for the passage of the aqueous humour are appropriate for this purpose. Braided materials are suitable, for instance, which are, on the one hand, permeable to water and present, on the other hand, the stiffness and resistance required for the aforementioned dilations.

Moreover, the small tube is open on its both ends. All the opening edges are extremely finely polished and rounded off. The used material must have a rigidity sufficient to prevent the canal from collapsing, and it must be entirely tolerable for the tissue in order to prevent wound-healing processes. An exemplary embodiment could be made of titanium, implant-quality steel electroplated with gold, or other materials.

A preferred improvement of the stent is provided with at least one additional smaller opening, preferably two openings, on the stent side turned away from the trabecular formations, in addition to at least one opening facing the trabecular formations and serving both as aperture for the outflow of aqueous humour and as passage opening for a micro-surgical instrument which can be longitudinally introduced into the stent and having a distal end that may be laterally guided through the passage opening inside the stent for projecting into the trabecular formations in order to create there mechanically minute ruptures in the trabecular formations. The openings, which present a smaller diameter and smaller dimensions than the outflow opening, are mainly intended to facilitate the maneuverability of the stent during its introduction into Schlemm's canal. To this end two openings are provided in the stent side by side and in direct opposition to the outflow opening. A retaining wire can be guided through the small openings from the rear side of the stent, with a loop forming inside the stent between the small openings. Both loose ends of the retaining wire project through the openings and towards the rear side of the stent, and may be seized by a holding and actuating instrument. The stent is seized with the holding and actuating instrument in such a way that the stent will be reliably and fixedly connected to it. In this manner it is now easily possible to introduce the stent through an appropriate opening into Schlemm's canal.

After the placement of the stent in Schlemm's canal the wire can be detached from the holding and actuating instrument and removed completely from the stent merely by threading out the wire by a loose end through the two small openings. The retaining wire introduced into the stent is provided, however, not only for a retaining function but also for an improved perforation or local severing of the trabecular formations as such. To this end the retaining wire is slightly released from its fixed connection with the holding and actuating instrument so that the wire loop, which is formed inside the stent between the two small openings, may be pushed into the interior of the trabecular formations opposite the outflow opening, in order to sever the tissue there locally. Whenever it will not or only insufficiently be possible to sever the tissue by means of the wire only it is possible to apply to the wire a suitable HF AC voltage, using an appropriate power supply, in order to achieve a desired increase of the permeability for the aqueous humour by way of severance of the tissue by coagulation.

This technique of mechanical local severance of the trabecular formations by means of a wire loop is particularly expedient for the reason that the configuration of the wire loop results in an inherent stability which cannot be achieved with a loose wire end possibly employed for similar purposes. Moreover, the reliability and safety of the operation is substantially increased by this provision.

In another alternative configuration, the stent is provided with only one smaller additional opening that is centered relative to the outflow opening. For handling the stent in its turn is wrapped with a wire loop, preferably in the area of its outflow opening, with the two loose wire ends being held by a holding and actuating instrument for controlled rough placement of the stent in Schlemm's canal. For precise centering of the stent inside Schlemm's canal a centering mandrel is provided that can be introduced into the smaller opening and hence serves for fine adjustment.

When the stent has been centered inside Schlemm's canal, the wire loop may be loosened and may additionally be used as cutting tool for severing, at least partly, the trabecular formations bearing against the stent. It is also possible to apply an HF voltage to the wire, which will contribute to an improved severance of the tissue in the trabecular formations.

BRIEF DESCRIPTION OF THE DRAWINGS

The invention will be described in the following by exemplary embodiments, without any restriction of the general inventive idea, with reference to the attached drawings wherein.

DESCRIPTION OF PREFERRED
EMBODIMENTS OF THE INVENTION

Figure 1A:
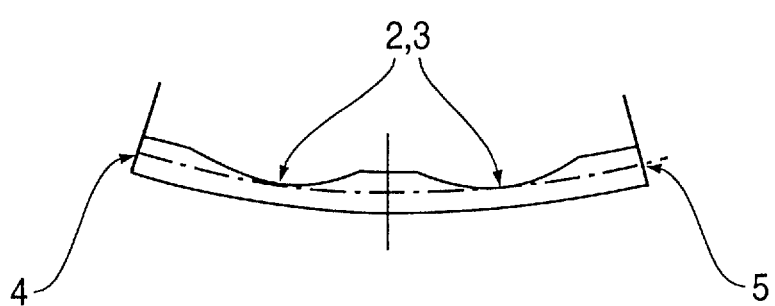
FIGS. 1a, b, c are views of three sides of a small tubular element configured in accordance with the present invention FIGS. 2a, b illustrate views showing the introduction of the small tubular element into Schlemm's canal, and FIGS. 3a, b show a small tubular element configured in accordance with the present invention, with openings for a retaining wire.

FIG. 1a illustrates a side view through the small tubular element 1. It presents a curvature along its longitudinal extension. Two openings 2, 3 are machined into the outside wall of the small tubular element 1 on the concave side. As is seen from FIG. 1, openings 2 and 3 have a smallest dimension corresponding to the inside diameter of the small tubular element 1 through which a surgical instrument can be longitudinally introduced. Two openings 4, 5 are provided on both sides on the end sections of the small tubular element.

All the edges of the openings 2, 3, 4 and 5 are extremely finely polished and rounded off in order to avoid any traumatic irritations of the tissue.

Figure 1C:
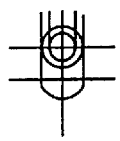

In the illustrated case, the internal diameter of the cross-sectional view illustrated in FIG. 1c amounts to 170 mm and its external diameter corresponds to 270 mm.

Figure 2A:
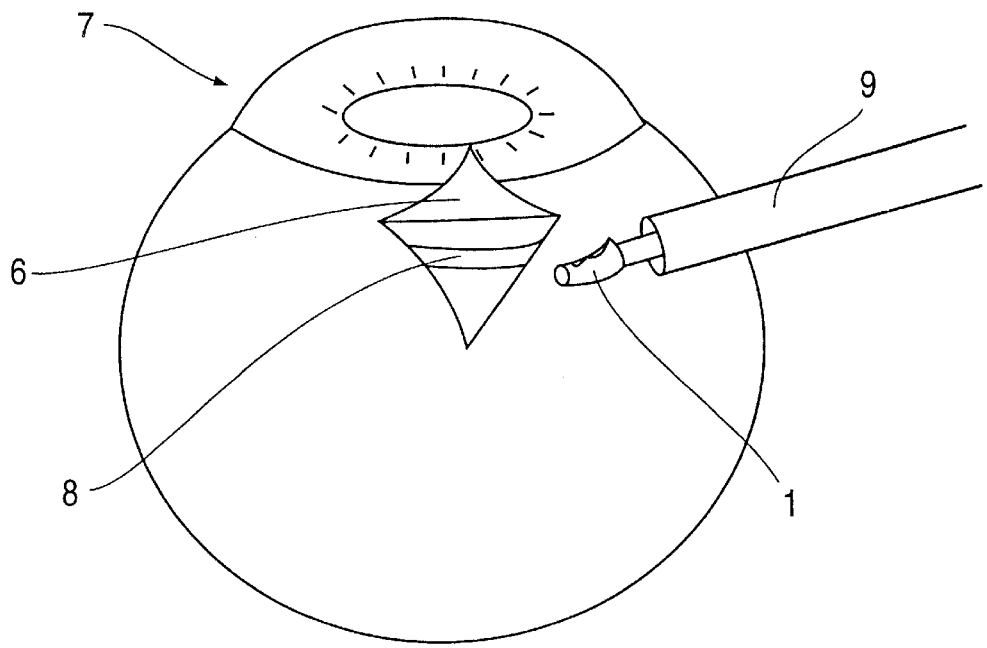

With application of an appropriate surgical technique, which is substantially the modification of the trabeculotomy technique as described above, Schlemm's canal is located and opened under a sciera lamella, the sclera 6 (cf. FIG. 2a) on the eye 7, from the outside. The small tube 1 (glaucoma stent) is the introduced into Schlemm's canal I' at placed at an appropriate site as required. To this end specifically manufactured introducing instruments 9 may be found helpful. Schlemm's canal 8 is then closed again while the sclera lamella is fixed again in its bed, which may be done either by suturing or by application of a tissue adhesive.

Figure 2B:
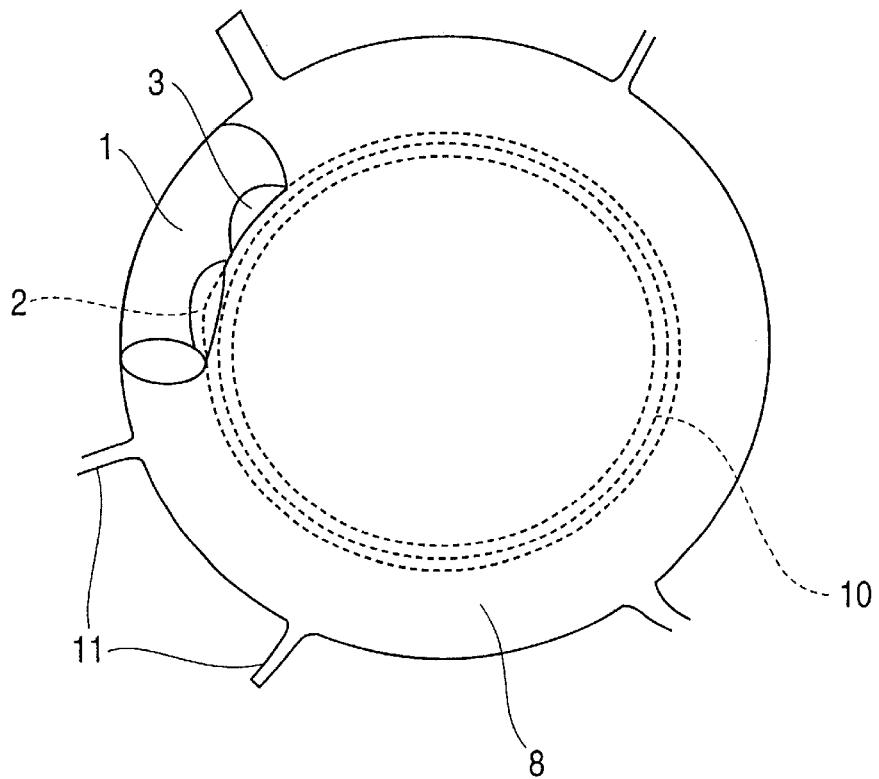

The intra-ocular pressure can now be reduced either merely as a result of the facts that the trabecular formations 10 (cf. FIG. 2b) are spread over the openings 2, 3 of the glaucoma stent 1 and that the meshwork 10 is consequently so dilated that the outflow obstruction will be reduced in this area to an extend sufficient to reduce the pressure.

When this is not the case, the trabecular formations 10 are opened via one or several openings located on the concave side of the stent or via one of the lateral openings of the stent, which may be done either by surgical means during the operation or by post-operative treatment, e.g. by disruptive laser application, or by means of any other conceivable methods.

The intra-ocular humour now gains access to the stent through these new openings so created, and to the entire circumference of Schlemm's canal and the natural excretory ducts 11 leading out therefrom via the two lateral openings 4, 5 of the stent, which are placed inside the intact part of Schlemm's canal 8. Wound healing entailing the closure of the opening cannot occur because the glaucoma stent prevents a collapse of the boundaries keeping the access to Schlemm's canal open.

Figure 1B:
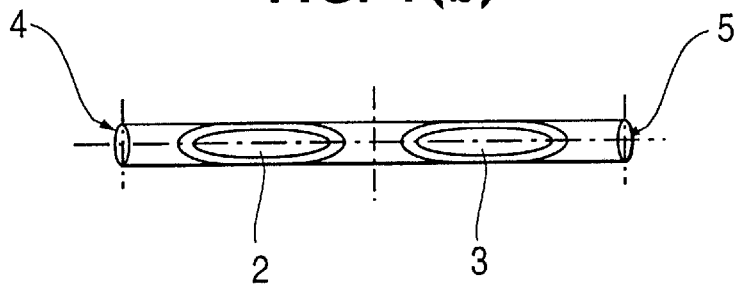
Figure 3A:
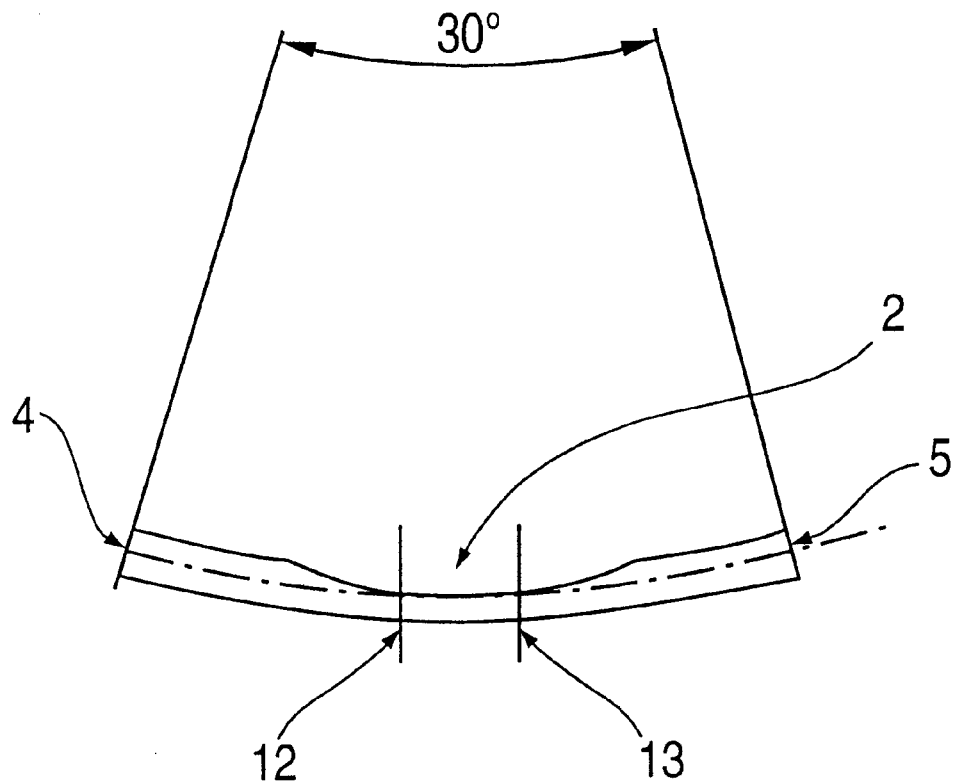
Figure 3B:
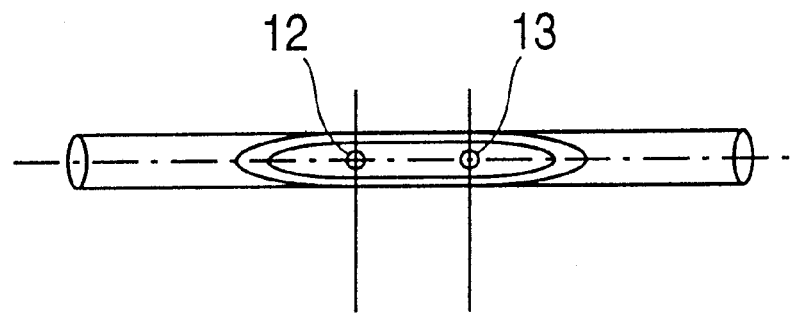

FIGS. 3a and b illustrate an improved embodiment of a stent in which two further small openings 12 and 13 are provided, in addition to the end openings in the embodiment according to FIG. 1, located on the outside of the stent, i.e. on the opening facing the opening 2. In distinction from FIG. 1, the stent of FIG. 3 is provided with only one opening 2 on the side facing the trabecular formations. As is seen from FIG. 1, openings and 3 have a dimension corresponding to the inside diameter of the small tubular element 1 through which a surgical instrument can be longitudinally introduced. The small openings 12, 13 are arranged side by side along the longitudinal extension of the stent (FIG. 3b) and have each a diameter in the range of one millimeter and less. A metal wire, which is not illustrated in FIG. 3 and which is preferably made of a material being a good conductor for electric current, is to be inserted through the openings and is guided through the openings 12 and 13 in such a manner that the wire will form a loop on the side of the concave curvature of the stent. The two loose ends of the wire open through the openings 12 and 13 on the side of the convex curvature where they are seized by an appropriate holding and actuating instrument (which is not illustrated).

The stent can be safely and reliably introduced into Schlemm's canal and positioned there for permanent placement by means of the holding and actuating instrument.

It is moreover possible to use the holding and actuating instrument in order to push the loop of the wire into the tissue region of the trabecular formations for local severance of the tissue there and for increasing in this manner the permeability of the trabecular formations for the aqueous humour, specifically in the immediate vicinity of the opening of the stent. It is furthermore possible to supply the wire with high voltage for optimization of the severing procedure inside the tissue. In this way it is possible to severe or perforate the tissue actually by a coagulating effect by means of a wire heated by high voltage. It is equally possible to push the wire, to which possibly a high-frequency voltage is applied, unilaterally through the opening into the trabecular formations in order to achieve, in this way, a perforation of this tissue region.

LIST OF REFERENCE NUMERALS 1 small tubular element, stent
2, 3 opening in the wall of the stent, facing the trabecular formations
4, 5 openings along the longitudinal extension of the stent
6 sclera
7 eye
8 Schlemm's canal (venous sinus of the sclera)
9 introduction instrument
10 trabecular formations
11 outflow path for the aqueous humour 12, 13 small openings

What is claimed is:

1. An implantable device for implanting into a human eye for improving permeability of ocular aqueous humour through trabecular formations into Schlemm's canal, comprising:
    a longitudinally curved tubular element including a wall enclosing a hollow duct with openings at opposed longitudinal ends thereof, at least one opening in a concave curvature of the wall, with a size and shape of the tubular element corresponding approximately to an internal contour Schlemm's canal, a material from which the wall is manufactured and a thickness thereof being selected so that upon implanting into Schlemm's canal and adjacent trabecular formations the tubular element expands Schlemm's canal and the adjacent trabecular formations and remains implanted inside Schlemm's canal; and wherein
    the at least one opening, has a smallest dimension corresponding to an inside diameter of the tubular element and through which a surgical instrument for creating perforations within the trabecular formations is passed.

2. A device according to claim 1, wherein:
the longitudinal curve of the tubular element corresponds approximately to a natural curvature of Schlemm's canal and dilates the trabecular formations, upon introduction into Schlemm's canal, and maintains Schlemm's canal open.

3. A device according to claim 2, wherein:
the at least one opening is machined into the wall material through which aqueous humour may laterally flow into the hollow duct.

4. The device according to claim 2, wherein:
the tubular element has an outside diameter in the range between 180 mm and 350 mm and an inside diameter between 150 mm and 200 mm.

5. A device according to claim 2, wherein:
the wall material is manufactured from a braided material and is permeable to the aqueous humour along all of the longitudinally curved tubular element.

6. A device according to claim 5, wherein:
the at least one opening is machined into the wall material through which aqueous humour laterally flows into the hollow duct.

7. A device according to claim 5, wherein:
the wall material consists of titanium, implant-quality steel electroplated with gold, or a synthetic compound material.

8. The device according to claim 7, wherein:
the tubular element has an outside diameter in the range between 180 mm and 350 mm and an inside diameter between 150 mm and 200 mm.

9. A device according to claim 7, wherein:
the at least one opening is machined into the wall material through which aqueous humour laterally flows into the hollow duct.

10. The device according to claim 5, wherein:
the tubular element has an outside diameter in the range between 180 mm and 350 mm and an inside diameter between 150 mm and 200 mm.

11. A device according to claim 2, wherein:
the wall material consists of titanium, implant-quality steel electroplated with gold, or a synthetic compound material.

12. The device according to claim 11, wherein:
the tubular element has an outside diameter in the range between 180 mm and 350 mm and an inside diameter between 150 mm and 200 mm.

13. A device according to claim 11, wherein:
the at least one opening is machined into the wall material through which aqueous humour laterally flows into the hollow duct.

14. A device according to claim 1, wherein:
the wall material is manufactured from a braided material and is permeable to the aqueous humour along all of the longitudinally curved tubular element.

15. A device according to claim 14, wherein:
the wall material consists of titanium, implant-quality steel electroplated with gold, or a synthetic compound material.

16. A device according to claim 15, wherein:
the at least one opening is machined into the wall material through which aqueous humour laterally flows into the hollow duct.

17. The device according to claim 15, wherein:
the tubular element has an outside diameter in the range between 180 mm and 350 mm and an inside diameter between 150 mm and 200 mm.

18. The device according to claim 14, wherein:
the tubular element has an outside diameter in the range between 180 mm and 350 mm and an inside diameter between 150 mm and 200 mm.

19. A device according to claim 14, wherein:
the at least one opening is machined into the wall material through which aqueous humour laterally flows into the hollow duct.

20. A device according to claim 1, wherein:

the wall material consists of titanium, implant-quality steel electroplated with gold, or a synthetic compound material.

21. The device according to claim 20, wherein:

the tubular element has an outside diameter in the range between 180 mm and 350 mm and an inside diameter between 150 mm and 200 mm.

22. A device according to claim 20, wherein:

the at least one opening is machined into the wall material through which aqueous humour laterally flows into the hollow duct.

23. The device according to claim 1, wherein:

the tubular element has an outside diameter in the range between 180 mm and 350 mm and an inside diameter between 150 mm and 200 mm.

24. A device according to claim 23, wherein:

the at least one opening is machined into the wall material through which aqueous humour laterally flows into the hollow duct.

25. A device according to claim 1, wherein:

the at least one opening is machined into the wall material through which aqueous humour laterally flows into the hollow duct.

26. A device according to claim 1, wherein:

all edges of the tubular element are polished and rounded off.

27. A device according to claim 1, wherein:

the tubular element has a cross-section of circular or triangular shape.

28. A device according to claim 1, wherein:

a length of the tubular element ranges from approximately 1 to 11 mm or 300 to 900 of a radian measure of Schlemm's canal having a circular extension.

29. The device according to claim 1, wherein:

the tubular element comprises at least one smaller opening in the wall with the concave curvature which is located so as to project within the at least one opening.

\* \* \* \* \*